United States Patent [19]

Winkelmann et al.

[11] 3,973,019
[45] Aug. 3, 1976

[54] PHARMACEUTICAL COMPOSITIONS CONTAINING 1,4-BIS-(5'-NITROIMIDAZOLYL-2'-METHYLENE-IMINO) PIPERAZINE COMPOUNDS FOR TREATING PROTOZOAL DISEASES AND METHODS FOR TREATING SUCH DISEASES

[75] Inventors: Erhardt Winkelmann, Kelkheim, Taunus; Wolfgang Raether, Dreieichenhain, both of Germany

[73] Assignee: Hoechst Aktiengesellschaft, Frankfurt am Main, Germany

[22] Filed: Dec. 20, 1974

[21] Appl. No.: 535,096

Related U.S. Application Data

[62] Division of Ser. No. 425,973, Dec. 19, 1973, Pat. No. 3,903,081.

[30] Foreign Application Priority Data

Dec. 21, 1972 Germany............................ 2262555

[52] U.S. Cl. ............................................. 424/250
[51] Int. Cl.² ...................................... A61K 31/495
[58] Field of Search ............................... 424/250

[56] References Cited
UNITED STATES PATENTS 3,752,809  8/1973  Rufer et al.......................... 424/250

*Primary Examiner*—Sam Rosen
*Attorney, Agent, or Firm*—Curtis, Morris & Safford

[57] ABSTRACT

1,4-bis-5'-nitroimidazolyl-2'-methylene-imino) piperazines of the formula

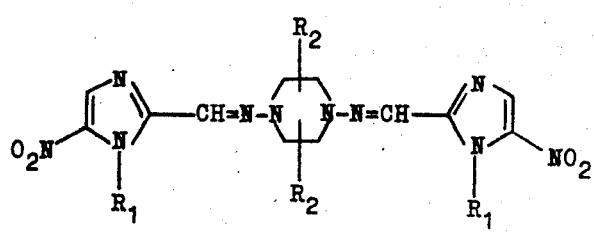

in which $R_1$ is hydrogen, methyl, ethyl or 2-hydroxyethyl and $R_2$ is hydrogen or methyl, are prepared by reaction of 5-nitro-imidazolyl-2-aldehydes or the functional derivatives thereof with 1,4-diamino-piperazines. Pharmaceutical compositions containing these compounds for treating protozoal diseases and methods of treating protozoal diseases with these compounds are disclosed.

10 Claims, No Drawings

PHARMACEUTICAL COMPOSITIONS CONTAINING 1,4-BIS-(5'-NITROIMIDAZOLYL-2'-METHYLENE-IMINO) PIPERAZINE COMPOUNDS FOR TREATING PROTOZOAL DISEASES AND METHODS FOR TREATING SUCH DISEASES

This is a divisional application of application Ser. No. 425,973 filed Dec. 19, 1973, now U.S. Pat. No. 3,903,081 granted Sept. 2, 1975.

The present invention relates to pharmaceutical compositions containing 1,4-bis-5'-nitroimidazolyl-2'-methylene-imino)-piperazines and to methods for treating protozoal diseases with said piperazine compounds.

1-Alkyl-5-nitro-imidazolyl-2-formyl-hydrazones are known according to German Offenlegungsschrift No. 1,595,928 to be active substances against protozoal diseases.

1-(2'-hydroxyethyl)-2-methyl-5-nitro-imidazole (Metronidazol) is used for the treatment of protazoal diseases, such as trichomoniasis and amebiasis.

An object of the present invention are bis-(5'-nitroimidazolyl-2'-methylene-imino) piperazines of the formula I

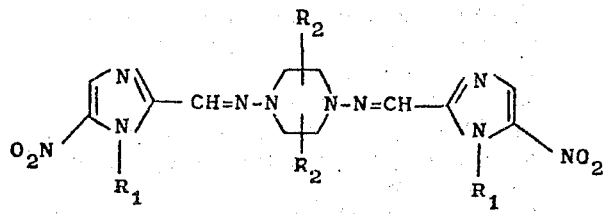

in which $R_1$ stands for a hydrogen atom, a methyl, ethyl or 2-hydroxy-ethyl group and $R_2$ for a hydrogen atom or a methyl group.

The novel compounds have a pronounced activity against trichomonads and amebiae, which is superior to that of the 5-nitro-imidazoles mentioned above.

A further object of this invention is a process for the manufacture of 1,4-bis-5'-nitroimidazolyl-2'-methyleneimino) piperazines of the formula I, which comprises reacting an 5-nitroimidazolyl-2-aldehyde of the formula II, or a functional derivative thereof,

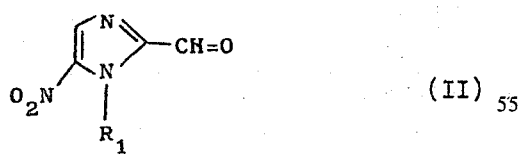

in which $R_1$ is defined as above, with a 1,4-diamino-piperazine of the formula III

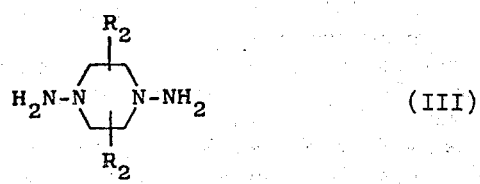

in which $R_2$ is defined as above.

The reaction is advantageously carried out using equimolar amounts of the reactants as well as a solvent or dispersing agent, preferably an alcoholic or aqueous solution or a mixture of an alcohol and water. The choice and the ratio of the solvents depend on the solubility of the compounds. As alcohols are used, for example, methanol, ethanol, propanol or isopropanol. The reaction temperature may be in the range of from 0° to 100°C, advantageously from 60° to 80°C. It is advantageous to add a small amount of an acid, for example hydrochloric acid or acetic acid, as a condensation catalyst. Depending on the reaction conditions used, the reaction times are in the range of from a few seconds to several minutes. In most cases, the reaction products are obtained in the form of crystals of high purity which are isolated in the usual manner by suction-filtration. Where required, they may be purified by recrystallization from a suitable solvent or mixture of solvents.

The 1,4-bis-5'-nitroimidazolyl-2'-methylene-imino) piperazines are suitable for the treatment of protozoal diseases in mammals as they are, for example, caused by infections with Trychomonas vaginalis and Entamoeba histolytica. The novel compounds of the invention may be administered orally or locally. For the oral route, the compounds are usually administered in the form of tablets or capsules containing, per daily dosage unit, about 10 to 750 mg of the active substance in admixture with a conventional diluent and/or excipient.

For local administration, jellies, creams, ointments or suppositories may be used.

In addition to a very good compatibility, the novel products according to the invention are distinguished by a safe activity against trichomonads and amebae, which is superior to the known pharmaceutical composition Metronidazol, as can be seen from the following Tables.

The following Examples serve to illustrate the invention.

EXAMPLE 1

(test for activity)

Activity against Trichomonas foetus was generally tested on home-bred albino mice (NMRI-strain) of both sexes. The body weight of each animal was from 10 to 12 grams.

The substance to be tested was administered orally by means of an esophagal sound either in an aqueous solution, or in the case of sparingly water-soluble compounds, in a Tylose suspension. The overall dosage was administered in two units, the first one two hours prior to infection and the second one two hours after infection. 4 Mice were used for each substance to be tested and for each dosage.

Infection was infective agents about by intraperitoneal injection of 19 million infectiveagents per animal in a suspension of 0.5 ml of a culture medium, Merck I. The standard Metronidazol was administered by the same route and in the same dosage as the substance to be tested (see Table 1).

As infection controls were generally used 10 mice which, after infection, were no longer treated. Another 5 mice served as a zero control (animals which were not treated and not infected).

Six days after infection, all the test animals were killed and the peritoneal exudate was examined for trichomonads. Mice which had died before were subjected to the same examination.

The test substance was judged on the concentration of infective agents to be found in the peritoneal exudate on the sixth day after infection. For this purpose, the concentration of infective agents established with the tested composition was compared to that of the standard and of the infection control. The scheme, according to which the tested substance and the standard were judged with regard to the concentration of infectants established, was the following:

ineffective:
Concentration of infectants was not substantially reduced as compared to infection control. Judgement: 3; 4 effective:
a. faint: Concentration of infectants moderately reduced as compared to infection control. Judgement: 2
b. unsatisfactory: Concentration of infectants substantially reduced as compared to infection control: Judgement: 1
c. no infective agents to be established. Judgement: 0

TABLE 1

| Composition | dosage in mg/kg mouse, per os | concentration of infectant Trichomonas foetus in 4 mice |
|---|---|---|
| I | 2 × 150 | 0 0 0 0 |
|  | 2 × 100 | 0 0 0 0 |
|  | 2 × 50 | 0 0 0 0 |
|  | 2 × 25 | 0 1 0 2 |
| II | 2 × 150 | 0 0 0 0 |
|  | 2 × 100 | 0 0 0 0 |
|  | 2 × 50 | 0 0 0 0 |
|  | 2 × 25 | 2 0 2 1 |
| infection controls | — | 4 4 4 4 |

I = product of the invention: 1,4-bis-(1'-methyl-5'-nitro-imidazolyl-2'-methylene-imino) piperazine
II = comparative composition: Metronidazol

EXAMPLE 2

(test for activity)

Activity against Entamoeba histolytica was generally tested on cross-bred gold hamsters of both sexes. The body weight of each animal was generally in the range of from 50 to 60 grams.

The substance to be tested was administered orally by means of an esophagal sound, either in an aqueous solution or, in the case of sparingly water-soluble compounds, in Tylose suspension. The overall dosage was administered in four units, the first one two hours prior to infection, the second one two hours after infection, the third one one day after infection and the fourth one two days after infection. 4 Hamsters were used for each substance to be tested.

Infection was brought about by intrahepatical injection of 130,000 infective agents per animal as a suspension in 0.1 ml of TTY medium (E. hist.-Crithidia culture). The standard Metronidazol was administered by the same route and in the same dosage as the substance to be tested (see Table 2.)

As infection controls were generally used 10 hamsters which were, after infection, not treated any more. Another 5 hamsters served as a zero control (animals which were not treated and not infected).

Six days at the earliest and eight days at the latest after infection, all the animals were killed. Subsequently, the liver's state was judged according to the degree of icteric necrosis developed. Hamsters which had died before were subjected to the same examination.

The liver findings as obtained with the tested composition and with the standard substance were compared to those of the infection controls. The scheme, according to which the liver findings (with tested composition and standard composition) were judged, was the following:

ineffective:
Icteric necrosis did not show any substantial difference from that of infection controls. Possible judgement: 3; 4 (in rare cases: 2), effective:
a. faint: Icteric necrosis was less developed than with the infection controls. Possible judgement: frequently 2 (in rare cases: 1),
b. unsatisfactory: Icteric necrosis was substantially reduced as compared to infection controls. Possible judgement: 0 (in rare cases), predominantly 1; 2 (in rare cases),
c. good: no iceteric necrosis was discovered. Judgement: 0

TABLE 2

| Composition | dosage in mg/kg gold hamster, per os | liver findings Entamoeba histo-lytica (extra-intestinal) in 4 gold hamsters |
|---|---|---|
| I | 4 × 150 | 0 0 0 0 |
|  | 4 × 100 | 0 0 0 0 |
|  | 4 × 50 | 0 0 0 0 |
|  | 4 × 25 | 0 1 0 0 |
| II | 4 × 150 | 0 0 0 0 |
|  | 4 × 100 | 0 0 0 0 |
|  | 4 × 50 | 0 1 0 2 |
|  | 4 × 25 | 3 0 3 2 |
| infection controls | — | 4 3 4 4 |

I = product of the invention: 1,4-bis-(1'-methyl-5'-nitro-imidazolyl-2'-methylene-imino)-piperazine
II = comparative composition: Metronidazol

EXAMPLE 3

(preparation of active substances)

1. 1,4-Bis-(1'-methyl-5'-nitroimidazolyl-2'-methylene-imino)-piperazine

A solution of 5.8 g (0.05 mol) of 1,4-diamino-piperazine in 70 ml of ethanol was added in one portion to a solution of 15.5 g (0.1 mol) of 1-methyl-5-nitro-imidazolyl-2-aldehyde in 70 ml of ethanol while some drops of glacial acetic acid were simultaneously added, and the reaction mixture was heated to 80°C for 5 minutes on a steam bath.

The final product precipitated at once in crystals which, after the solution had been cooled, were suction-filtered, washed with some cold water, ethanol and ether and dried. 15.4 g of bis-(1'-methyl-5'-nitroimidazolyl-2'-methylene-imino) piperazine were obtained (corresponding to 79 % of the theoretical yield) in the form of ochre-colored fine crystals which decomposed at 268°C.

In the same manner as disclosed above, the following compounds could be prepared:

2. 1,4-bis-[1'-(2''-hydroxyethyl)-5'-nitroimidazolyl-methylene-(2')-imino] piperazine which decomposed at 187°C, and
3. 1,4-bis-(1'-methyl-5'-nitroimidazolyl-2'-methylene-imino)-2,6-dimethyl-piperazine which decomposed at 245°C.

Preparation of the starting substances:

1-Methyl-5-nitro-imidazolyl-2-aldehydes of the formula II were obtained by oxidation of 1-methyl-2-hydroxy-methyl-5-nitro-imidazoles with manganese dioxide (cf. German Offenlegungsschrift No. 1,595,928). The hydroxy methyl compound was obtained by hydroxymethylation of 1-methyl-5-nitroimidazole (cf. German Offenlegungsschrift No. 1,470,102).

Further starting substances of the formula II were the following aldehydes and their functional derivatives: 1-Methyl-5-nitro-imidazolyl-(2)-aldehyde, 1-ethyl-5-nitro-imidazolyl-(2)-aldehyde or 1-(2'-hydroxyethyl)-5-nitro-imidazolyl-(2)-aldehyde as well as the mono- and diacetals, the mono- and dimercaptals and the corresponding mono- and diacetates thereof; moreover, correspondingly substituted aldimines, oximes, hydrazones, semicarbazones, thiosemicarbazones and the corresponding aldehyde-cyano-hydrines or hydrogeno-sulfite compounds.

1,4-Diamino-piperazines of the formula III used as starting substances were obtainable according to Berichte 24, 3245.

What is claimed is:

1. A pharmaceutical composition for the oral treatment of protozoal diseases caused by *Trichomonas vaginalis* or *Entamoeba histolytica*, which composition comprises from about 10 mg to about 750 mg per dosage unit of a 1,4-bis-(5'-nitroimidazolyl-2'-methylene-imino) piperazine of the formula

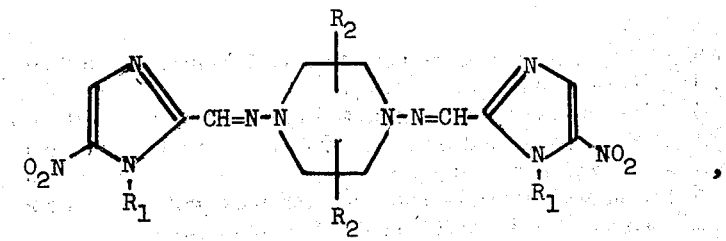

wherein $R_1$ is hydrogen, methyl, ethyl, or 2-hydroxyethyl and $R_2$ is hydrogen or methyl, in admixture with a pharmaceutical excipient.

2. A pharmaceutical composition as defined in claim 1 in which the piperazine compound is 1,4-bis-(1'-methyl-5'-nitroimidazolyl-2'-methylene-imino)piperazine.

3. A pharmaceutical composition as defined in claim 1 in which the piperazine compound is 1,4-bis-[1'-(2''-hydroxyethyl)-5'-nitroimidazolyl-2'-methylene-imino]piperazine.

4. A pharmaceutical composition as defined in claim 1 in which the piperazine compound is 1,4-bis-(1'-methyl-5'-nitroimidazolyl-2'-methylene-imino)-2,6-dimethyl piperazine.

5. A pharmaceutical composition for local administration for the treatment of protozoal diseases caused by *Trichomonas vaginalis* or *Entamoeba histolytica*, which composition comprises a jelly, cream, ointment, or suppository containing an effective amount of a 1,4-bis-(5'-nitroimidazolyl-2'-methylene-imino) piperazine of the formula

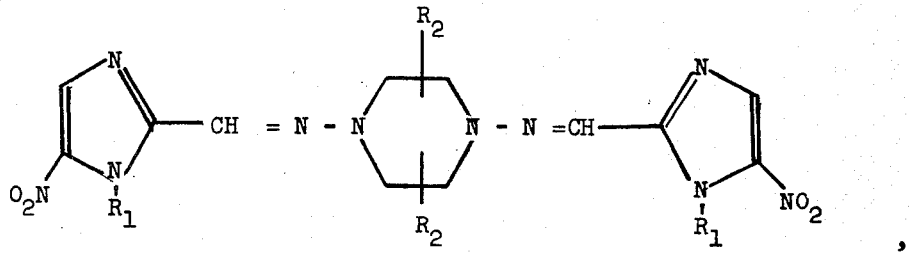

wherein $R_1$ is hydrogen, methyl, ethyl, or 2-hydroxyethyl and $R_2$ is hydrogen or methyl.

6. A method for treating protozoal diseases caused by *Trichomonas vaginalis* or *Entamoeba histolytica*, which method comprises administering an effective amount of a 1,4-bis-(5'-nitroimidazolyl-2'-methylene-imino) piperazine of the formula

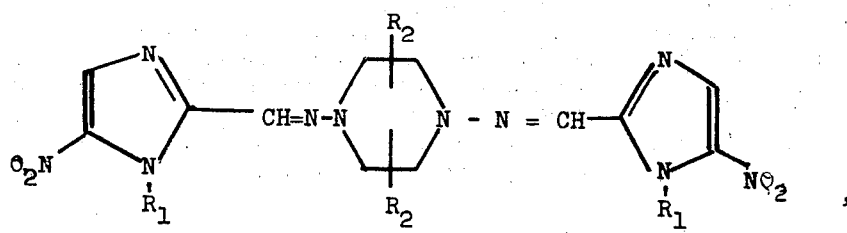

wherein $R_1$ is hydrogen, methyl, ethyl, or 2-hydroxyethyl and $R_2$ is hydrogen or methyl.

7. A method as defined in claim 6 which comprises oral administration of a daily dosage of about 10 to 750 mg of said piperazine compound.

8. The method defined in claim 7 in which the piperazine compound is 1,4-bis-(1'-methyl-5'-nitroimidazolyl-2'-methylene-imino)piperazine.

9. The method defined in claim 7 in which the piperazine compound is 1,4-bis-[1'-(2''hydroxyethyl)-5'-nitroimidazolyl-2'-methylene-imino]piperazine.

10. The method defined in claim 7 in which the piperazine compound is 1,4-bis-[1'-methyl-5'-nitroimidazolyl-2'-methylene-imino]-2,6-dimethyl piperazine.

* * * * *